United States Patent [19]

Drisaldi et al.

[11] Patent Number: 4,523,908
[45] Date of Patent: Jun. 18, 1985

[54] DEVICE FOR POSITIONING AND PROTECTING AN ORTHODONTIC BRACKET

[76] Inventors: Giovanni Drisaldi, Via Valletta Fogliano, 1; Eugenio Fontana, Via S. Giovanni 89/14, both of I - 27029 Vigevano; Virgilio Manetti, Via Filagno, 14, I - 24047 Treviglio; Franco Segù, Corso Cavour, 34, I - 27029 Vigevano; Sandro Segù, Corso Cavour, 102, I - 27029 Vigevano; Bruno Segù, Via Trilussa, 22, I - 27029 Vigevano, all of Italy

[21] Appl. No.: 625,174

[22] Filed: Jun. 25, 1984

Related U.S. Application Data

[63] Continuation of Ser. No. 529,984, Sep. 8, 1983, abandoned, which is a continuation of Ser. No. 339,161, Jan. 13, 1982, abandoned, which is a continuation of Ser. No. 193,007, Oct. 2, 1980, abandoned.

[30] Foreign Application Priority Data

Dec. 7, 1979 [IT] Italy .................. 27918 A/79

[51] Int. Cl.³ .............................................. A61C 7/00
[52] U.S. Cl. ................................................ 433/8; 433/3
[58] Field of Search ....................... 433/3, 8, 2, 16

[56] References Cited

U.S. PATENT DOCUMENTS 4,014,096  3/1977  Dellinger .................. 433/3
4,134,208  1/1979  Pearlman .................. 437/8

Primary Examiner—Robert Peshock
Attorney, Agent, or Firm—Young & Thompson

[57] ABSTRACT

The invention relates to a device, preferably of disposable type, for application to orthodontic brackets for retaining an orthodontic harmonic wire, either said brackets are of the type welded to an orthodontic band, or of the type supported on a plate for direct fastening. The device serves the purpose of facilitating the positioning of said orthodontic brackets on teeth, at a predetermined distance from the incisal edge thereof, and protecting the bracket from the entrance of the fastening cement, such a bracket having the slot and hooks for the binding of the orthodontic wire. The device comprises a shell part forming a housing for the slot element of the bracket, and a positioning part made to predetermined size and suitable to bear on the incisal edge of the tooth.

1 Claim, 5 Drawing Figures

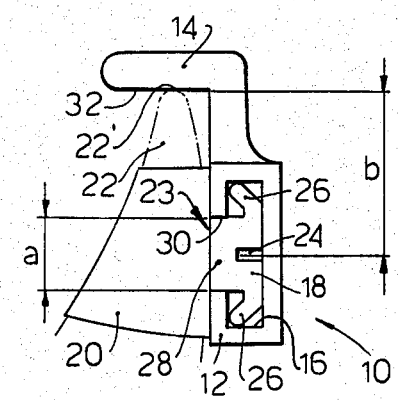
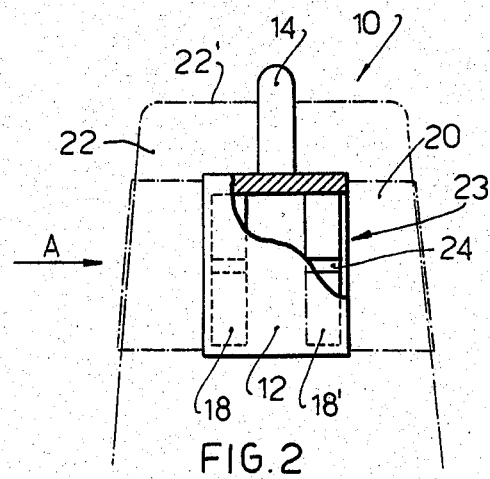
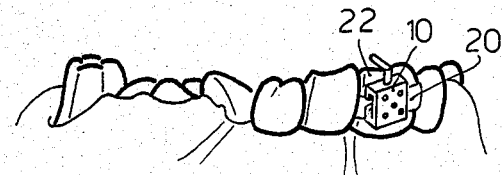
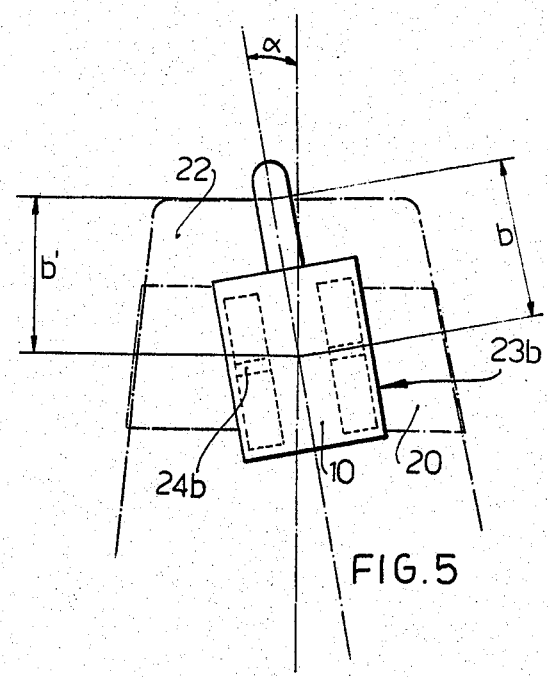
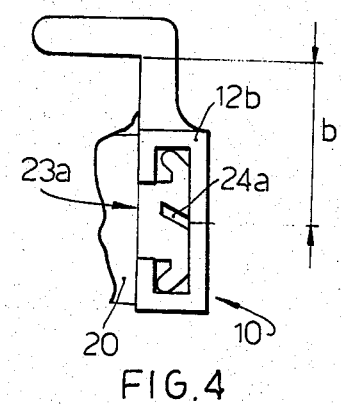

DEVICE FOR POSITIONING AND PROTECTING AN ORTHODONTIC BRACKET

This application is a continuation of Ser. No. 529,984 filed Sept. 8, 1983 and now abandoned, which is a continuation of Ser. No. 339,161 filed Jan. 13, 1982, also abandoned, which is a continuation of Ser. No. 193,007 filed Oct. 2, 1980 and also abandoned.

This application relates to the field of devices for orthodontia.

At present, in order to straighten, level or flush, or in any case to correct wrong positions of teeth in a mouth, the use is made of an orthodontic wire which is particularly bent and curved to positions corresponding to each tooth, so as to exert on each said tooth the proper action of torsion, pressure, etc. The orthodontic wire is anchored to the tooth by means of a connection generally referred to as a bracket, which may comprise a metal band surrounding the tooth, or a small plate. The connection carries a raised element forming a window (generally referred to as a slot) for the passage of the orthodontic wire, and hooks or notches for binding said wire by means of a fastening wire. The slot element may be in a single part, or two side by side or juxtaposed parts, and in such a case the connection would be referred to as twin bracket. The band or small plate is secured to the respective tooth by suitable cement at a position which should be strictly determined.

The bracket positioning with respect to the tooth is carried out by reference to the incisal edge of the tooth.

According to a technique as used at present, such a positioning was provided by means of fixed gauges, having one peak bearing on the incisal edge of the tooth, and one other peak entering into slot. Moreover, such gauges had to be manually held during the time required for cementing said bracket to the tooth. The operation was unaccurate, arduous and uncomfortable. Furthermore, the known gauges were expensive and it was required to have a large number of gauges in stock in order to allow the variety of distances from the incisal edge required, depending on the tooth to which the bracket is applied. Further again, since the gauges had to be reused, such gauges usually would pass from the mouth of one patient to the mouth of another patient, and accordingly had to be thoroughly sterilized each time.

In the technique as far being used, still another disadvantage consists in the cement used for securing the bands or small plates to the teeth often soiling the connection slots and, accordingly, the latter had to be cleaned prior to application of the orthodontic wire.

Therefore, the scope of the invention is to overcome the above mentioned disadvantages.

Thus, the device according to the present invention was developed, such a device comprising a shell portion for protecting the slot as the cement is being applied, and an integral positioning portion in the form of a bent arm to assure a predetermined distance for the slot from the incisal edge of the tooth. The shell portion has fixed dimensions and can be equally well applied to each type of bracket at present commercially available. The device is made in a plurality of versions, with different size for the spacing arm, depending on the tooth to which the connection as to be applied. The device is made of plastics material, of a highly reduced cost and accordingly of disposable type, and assures the highest degree in hygiene. It is used by inserting the shell portion thereof on the bracket and bearing the spacing arm of the device on the incisal edge or top of the tooth. Therefore, the use of the device is of extreme easiness and accuracy and the use thereof enables to protect the connection slot against any cement intrusion.

The device according to the invention will now be hereinafter described in further detail with reference to the accompanying drawings, in which:

FIG. 1 is a side view of the device, as inserted on a bracket applied to a tooth (shown by dash-dot line);

FIG. 2 is a front view of the device, as seen from the right in FIG. 1, and with a part broken away to show the underlying portion;

FIG. 3 is a perspective view, on a different scale from that of FIGS. 1 and 2, showing a device applied to a bracket mounted on an incisive tooth;

FIG. 4 is similar to FIG. 1, but showing the device as applied to a bracket provided with angled slot; and FIG. 5 is similar to FIG. 2, and shows the device as applied to a connection provided with inclined slot.

In the figures of the accompanying drawings, the new device has been designated as a whole at 10. The device comprises a shell portion 12 and a positioning portion 14, firmly integral to each other. The shell portion 12 forms a housing 16 of a size for accomodating the slot element 18 of an orthodontic bracket 23. In the case shown in the drawing, the latter is a bracket welded to a band 20, that is comprises a band 20 surrounding the tooth 22 to which is cemented. The device can be applied as well to brackets without band, preset for tooth fastening either according to direct or indirect technique.

As shown in the figures of the accompanying drawings, the whole slot element 18 is received within said housing 16, and thus the device covers and protects the slot 24 for the passage of the orthodontic wire (not shown) and the hooks 26 for securing said orthodontic wire; whereas the neck portion 28 of the slot element 18 is received with sufficient precision within the device aperture 30, connecting said housing 16 with the outside. It should be noted that the dimensions of said neck portion 28 are the same for brackets 23 of various types, used for several orthodontic techniques and made by different firms so that, by providing a protective device with housing 16 of sufficient length and dimension a of aperture 30 so as to be arranged by slight force fitting about the neck 28, the device 10 can be adapted with sufficient accuracy to all brackets 23 as commercially available at present. As shown in FIG. 2, the shell 12 as seen in front view has a sufficient extension to cover or bridge the two slot elements 18, 18' of a twin bracket, while being obviously applicable also to a non-twin bracket.

The positioning portion 14 is integral with the shell portion 12, and comprises a bent arm, so as to form a reference surface 32, intended to bear on the incisal edge 22' of tooth 22 (or in the case on the peak of a tooth). The distance or spacing b, from said slot 24 to said reference surface 32, should be accurately determined.

According to the present invention it is contemplated to preferably provide devices 10 of four types, with a distance or spacing b respectively of 3.0 mm, 3.5 mm, 4.0 mm and 4.5 mm, depending on the tooth to which the connection or bracket is to be applied (for instance, for an incisive tooth, a device having a distance or spacing of 3 mm will be used). A universally understandable code indication, for the type of device (that is for the relative distance or spacing b), could be shown on the front face of the device, such as shown for example in FIG. 3, by dots in a particular arrangement, or by various colours.

The device is preferably made of molded plastics material, such as ABS (acrylonitrile-butadiene-styrene), and therefore can be marketed at a low cost, so that it can be used as disposable device, with evident advantages as to hygiene.

The device is used as hereinafter explained.

Depending on the tooth to which the bracket has to be applied, the suitable size of the device is selected, and the device is inserted by causing it to slide over the slot element in the direction of arrow A (see FIG. 2), to cover the element or elements 18, 18' forming the slot 24. Then, (FIG. 3) the bracket with said device 10 applied is caused to bear on the tooth, until the surface 32 of arm 14 is brought to bear on the incisal edge or top of the tooth; thus, the accurate location on the tooth is provided for the bracket 23, which can be cemented. Since the slot 24 and hooks 26 are covered by the shell portion 12 of the device, there is no risk of soiling thereof with the cement. Upon cementing operation completion, the device 10 is removed by any suitable tool, leaving the slot and hooks in view or exposed.

The device may be used as well also in case of brackets 23a provided with angled slot 24a, as shown in FIG. 4, or brackets 23b provided with inclined slot 24b as shown in FIG. 5. Thus, in the case of FIG. 4, the center line of the shell portion 12 of the device is still corresponding to the axis of the inlet to slot 24a, the positioning at a distance "b" from the tooth edge being accomplished relative thereto. In the case of FIG. 5, by using the device 10, the average distance or spacing of the axis of the inclined slot 24b from the incisal edge would be "b'" instead of "b", but for rather small angles the difference would be negligible.

Of course, changes and modifications can be made to the device as far described, and it should be understood that all of the changes and modifications in the range of those skilled in the art are within the field or scope of the present invention.

What I claim is:

1. A one-piece disposable plastic device for applying, to a tooth, an orthodontic bracket provided with at least one slot for receiving an orthodontic wire for orthodontic use, comprising a positioning portion in the form of a small round rod at one end of said device having a rounded positioning surface on one side thereof that bears directly on the incisal edge or top of a tooth and having an opposite surface on the other side thereof that is an extreme end surface of said device, and located at a predetermined distance relative to the axis of said slot, and at the other end of said device a shell portion for covering said slot, said shell portion having a flat upright surface against which said slot opens, said two portions being integral with each other and having a total length less than the exposed height of a tooth, said shell portion having a housing of sufficient size to receive the element or elements of the bracket provided with slot, and the hooks for the fastening of the orthodontic wire, said shell having an aperture for the passage of the neck joining said bracket to the tooth or to the band, said aperture being of such size as to accurately accommodate said neck with slight force fitting about said neck and with the surfaces of the shell and neck that are next to the tooth substantially flush with each other.

* * * * *